United States Patent [19]

Baker et al.

[11] 4,123,932
[45] Nov. 7, 1978

[54] DOSIMETER FOR MONITORING WORKING AREAS

[75] Inventors: William B. Baker, Newark; Donald G. Clark, Wilmington, both of Del.

[73] Assignee: E. I. Du Pont de Nemours and Company, Wilmington, Del.

[21] Appl. No.: 800,430

[22] Filed: May 25, 1977

[51] Int. Cl.² ............................................. G01N 1/24
[52] U.S. Cl. ..................................................... 73/28
[58] Field of Search ................. 73/23, 28, 421.5 R, 73/421.5 A; 417/43, 44, 45, 12

[56] References Cited

U.S. PATENT DOCUMENTS

| | | | |
|---|---|---|---|
| 1,910,202 | 5/1933 | Crago | 417/43 |
| 2,889,780 | 6/1959 | Binford | 417/43 |
| 2,982,131 | 5/1961 | Rosinski | 73/421.5 R |
| 3,129,587 | 4/1964 | Hallanger | 73/211 |
| 3,410,059 | 11/1968 | Garnier | 73/23 |
| 3,411,704 | 11/1968 | Hilgert et al. | 417/280 |
| 3,424,370 | 1/1969 | Law | 415/1 |
| 3,501,899 | 3/1970 | Allen | 417/43 |
| 3,537,296 | 11/1970 | Gamache | 73/23 |
| 3,701,280 | 10/1972 | Stroman | 73/23 |
| 3,726,607 | 4/1973 | Garman | 417/12 |
| 3,748,906 | 7/1973 | Manka | 73/421.5 A |
| 3,784,902 | 1/1974 | Huber | 73/23 |
| 3,865,512 | 2/1975 | Deters | 417/44 |
| 3,882,861 | 5/1975 | Kettering et al. | 417/44 |
| 3,949,734 | 4/1976 | Edwards et al. | 417/43 |
| 3,953,152 | 4/1976 | Sipin | 417/45 |
| 3,956,940 | 5/1976 | Guild | 73/28 |
| 3,989,913 | 11/1976 | Lundquist et al. | 417/12 |

*Primary Examiner*—Stephen A. Kreitman

[57] ABSTRACT

An improved dosimeter for monitoring working areas in which air, preferably in a relatively large volume, is pumped through the dosimeter at a controlled constant flow and any particles or vapors in the air are collected on a filter, the improvement is the use of a variable drive pump connected to the filter and driven by an electric motor and controlled by a feed back circuit of an integrator and an amplifier and the pump maintains a constant flow of air through the dosimeter;

in the operation of the dosimeter the integrator receives a signal from a pressure switch that detects changes in the flow of the air stream through the dosimeter by a change in a pressure drop of the air which is being pumped through an orifice;

the dosimeter is placed in a work area and at the termination of a period of time, such as a work day, the filter is removed and the contents collected are analyzed by conventional techniques such as gas chromatography to determine a level of exposure of individuals working in that area.

11 Claims, 4 Drawing Figures

DOSIMETER FOR MONITORING WORKING AREAS

BACKGROUND OF THE INVENTION

This invention relates to a dosimeter and in particular to a dosimeter designed for monitoring working areas.

Dosimeters are known and have been used in an effort to determine the level of exposure of workers to foreign substances in air, for example, to chemical vapors or fumes, dust particles and the like. A dosimeter is placed in a work area and air is pumped through a filter which traps foreign substances in the air. At the end of an exposure period, the filter is removed and analyzed for any foreign substances. One problem with these dosimeters has been that the air flow rate through the dosimeter has not been accurately controlled at a constant flow rate. For example, if the filter is partially blocked so that intake of air is momentarily stopped or reduced for a period of time, it is not possible to adjust and increase the flow rate of air to compensate for the stoppage or reduction of air passing through the filter of the dosimeter. Any reduction in the air flow rate reduces the amount of foreign substances collected by the filter thereby giving an inaccurate reading.

SUMMARY OF THE INVENTION

An improved dosimeter for monitoring working areas has a filter means, an electric motor, a power source and an exhaust port in which particles or vapors in an air stream pumped through the dosimeter are collected on the filter means; the improvement that is used therewith to provide a controlled constant flow rate of the air stream through the dosimeter comprises
   a variable drive multicylinder pump, tubularly connected to the filter means and coupled to the electric motor, draws the air stream through the filter means;
   an orifice positioned in a tube attached to the pump and to the exhaust port wherein the air stream is pumped through the orifice by the pump and thereby creates an air pressure drop which varies with the flow of the air stream;
   a differential pulsation filter positioned in a tube connected to the exhaust port and in parallel with the orifice and reduces pulsations in the air stream;
   a differential pressure switch positioned in a tube connected in parallel to the differential pulsation filter that is activated by a change in the air pressure drop of the air stream and creates a low voltage electrical input signal;
   an integrator circuit electrically connected to the power source and to the pressure switch uses the low voltage input signal generated by the pressure switch is fed integrates this signal; and
   an amplifier circuit electrically connected to the power source and connected in series to the integrator circuit and to the electric motor which amplifies the signal generated by the integrator circuit and feeds this amplified signal to the electric motor, thereby controlling the speed of the motor, driving the pump in relationship to the signal generated by the pressure switch, to maintain the air stream at a controlled constant flow rate.

DETAILED DESCRIPTION OF THE INVENTION

The dosimeter is about 4 inches × 5 inches × 2¼ inches. The dosimeter is rugged in design and of reasonable cost and well suited for industrial use.

The dosimeter is placed in a work area to monitor the environment to which workers are exposed. After the dosimeter is operated for a period of time, usually an 8 hour shift, the filter is removed and the contents of the filter are analyzed.

Figure 1:
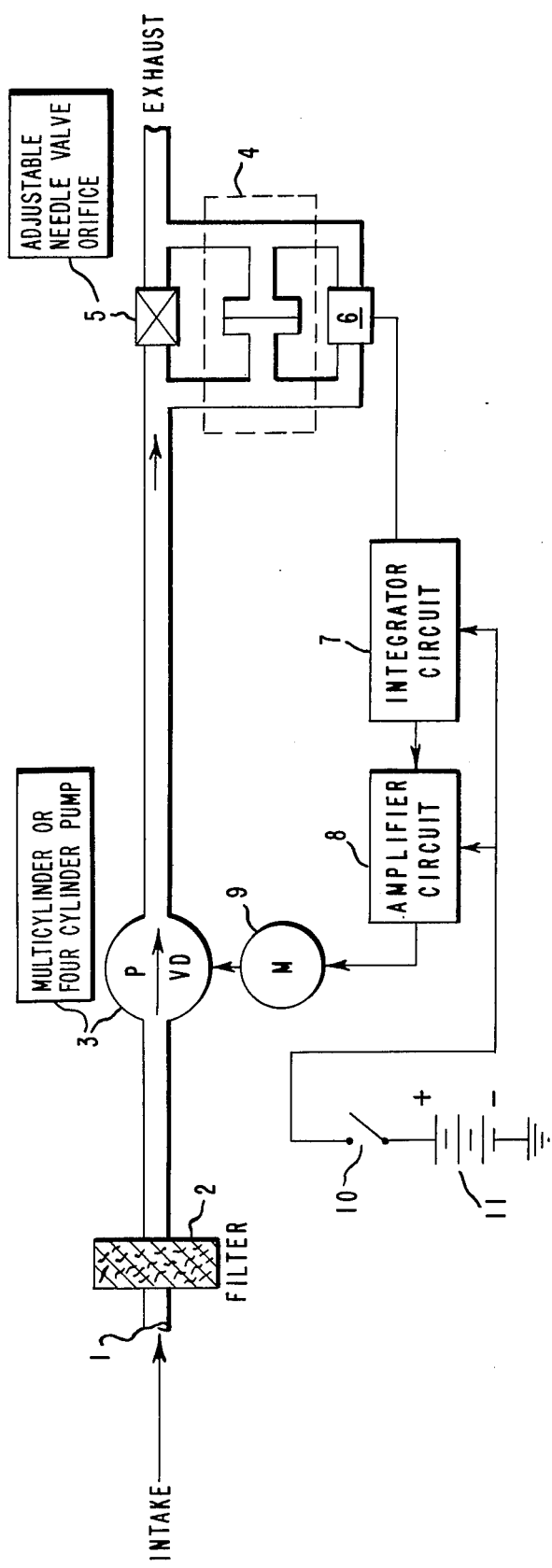
FIG. 1 is a diagram of the dosimeter.

Referring to the diagram of FIG. 1, a basic arrangement of the area dosimeter is shown. Air is pumped in at the intake 1 at a constant flow rate and passed through a filter 2. The air intake and filter are connected by a tube to a variable drive multicylinder air pump 3 driven by an electric D.C. motor 9. The air is pumped through an orifice 5 positioned in tube leading to the exhaust port that causes an air pressure drop. A differential pulsation filter 4 is positioned in a tube connected to the exhaust port and in parallel with the orifice 5. A pressure switch 6 is positioned in parallel to the differential pulsation filter and is activated by any change in the air pressure drop. The pressure switch 6 is electrically connected to the integrator circuit 7 which utilized the input from the pressure switch and generates an electrical signal. The signal generated by the integrator 7 is fed to the amplifier circuit 8 which amplifies the signal and the signal controls the speed of the electric motor 9 driving the pump 3 to provide a controlled constant flow rate of air through the dosimeter. The integrator and the amplifier are electrically connected to a D.C. power source 11 which usually is a battery. An on-off switch 10 is positioned between the power source 11 and the amplifier and integrator circuits.

Configuration other than the above for the dosimeter can be used. For example, the orifice can be tubularly connected in series to the filter and the pump. The pump draws an air stream through the orifice and through the filter. As above, a pulsation filter and a pressure switch are in parallel relationship to the orifice and the switch measures any change in an air pressure drop. In another example, a filter and orifice are tubularly connected in series to a pump and the pump draws the air through the filter and orifice. A pulsation filter and a pressure switch are positioned in parallel to the orifice and the switch measures any change in an air pressure drop. In any of the above configurations, the dosimeter would operate without the pulsation filter but the life of the pressure switch would be substantially shortened. Also, in any of the above configurations, the flow rate of the air stream is determined by the size of the opening in the orifice and the pressure required to actuate the pressure switch.

The filter 2 of the dosimeter can be adapted to entrap almost any type of substance such as gases, liquids or solids. If mechanical filtration is only required, for example, to collect dust particles to which a worker is exposed, a filter is provided which will entrap particles of 0.01 microns or larger. If the filter is to entrap a gas such as sulfur dioxide, a chemical filter is used which will entrap this gas. If vapors are to be entrapped, then a filter such as a charcoal filter, is used which entraps vapors. At the end of a period, such as an 8-hour shift, during which the dosimeter is in use monitoring an area, the filter is removed and examined for the substance or substances which were present in the work area. A simple count of particles under a microscope may be used or the filter can be analyzed, for example, with a gas chromatograph or weight increase by a gavimetric analyzer.

A variable drive multicylinder air pump is used in the dosimeter. Generally, a four cylinder diaphragm pump is used that pumps from about 5 to 10,000 cubic centimeters of air per minute at a continuous or nearly continuous flow. The pump is electrically connected to a conventional D.C. motor of about 0.0001 - 0.1 horsepower. The motor is a variable speed motor and operates from about 5 to 10,000 revolutions per minute. Usually a belt is used to connect the motor to the pump; using an arrangement of pulleys, by changing the size of the various pulleys, the speed of the motor can be changed. An advantage of a belt and pulleys is that the belt will slip if the pump becomes restricted and no damage to the motor will result. The motor can also be connected directly to the pump or connected by gears to the pump.

An orifice valve is positioned in a tube connecting the pump to the exhaust port. The orifice creates a pressure drop in the air stream of about 0.3 - 10 inches of water. Usually a pressure drop of about 3 inches of water is used and correspondingly, a pressure switch with a set point of 3 inches of water is used therewith. A fixed or an adjustable orifice can be used. A typical adjustable orifice which preferably is used is an adjustable needle valve. Examples of fixed orifices are a venturi tube and a plate with a hole of the desired size.

Figure 2:
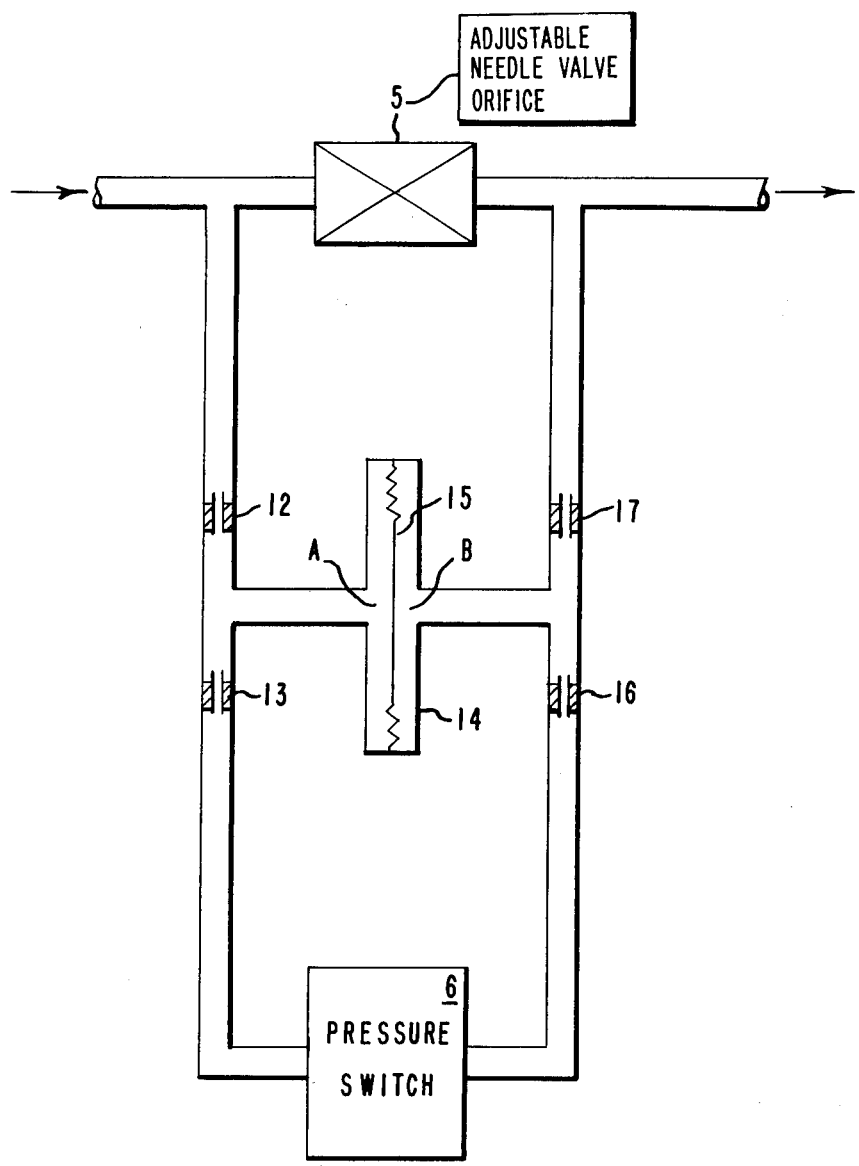
FIG. 2 is a diagram of the differential pulsation filter.

The differential pulsation filter eliminates pressure surges in the air stream caused by the pump so that the pressure switch does not operate on each pressure surge generated by each pump stroke but operates on the average pressure drop across the orifice thereby extending the life of the pressure switch. The pulsation filter also causes a delay of the pressure signal traveling to the pressure switch. This delay caused the circuitry controlling the pump to increase the speed or slow the speed of the pump in a repeatable manner. FIG. 2 shows the elements of the differential pulsation filter. The air from the pump flows through the orifice 5. A pressure drop across the orifice 5 is created which generates a higher pressure on the inlet than on the exhaust side of the orifice 5. The higher pressure is transmitted to the pressure switch through orifices 12 and 13 which reduce surges in the air stream. A pressure surge in the air stream on the inlet side of the orifice 5 first passes through orifice 12 and fills the A compartment of the accumulator chamber 14. In this chamber, a flexible diaphragm 15 allows considerable volume change before sufficient pressure builds up and forces the flow of air through orifice 5. The surge coming into compartment A causes the diaphragm 15 to move which in turn generates a pressure pulse in compartment B, or the other side of the diaphragm 15 and starts this smaller pulse flowing through orifice 16 to the low side of the pressure switch 6. This action substantially reduces the surge on the high pressure side of pressure switch 6 which has been further moderated by orifice 13. The exhaust side of the orifice 5 must be connected to the low side of the pressure switch so that the pressure switch 6 can operate in a differential mode. The connection to the low pressure side of the pressure switch 6 is made through orifices 16 and 17 to further reduce surges generated across the orifice 5. Thus the differential pulsation filter moderates the air pressure surges in the air stream and provides a relatively constant level of pressure to the pressure switch which represents the average of the pressure drop generated across orifice 5 and allows for smooth and continuous operation of the air pump since the signal generated by the pressure switch is utilized by the integrator circuit to control the operation of the air pump.

Generally, a differential pressure switch is used that has a set point that is about the same as the pressure drop across the orifice and that is sensitive to a pressure drop change in the air stream of about 0.01 - 0.5 inches of water. The sensitivity of the switch or the amount of pressure required to activate the switch determines the number of signal changes fed to the integrator. A switch having a low level of sensitivity would feed fewer on-off changes of signal to the integrator than would a switch of high sensitivity. A switch with a fixed level of sensitivity or a switch with an adjustable level of sensitivity can be used.

As pointed out above, the flow rate of the air stream is determined by the size opening in the orifice and by the sensitivity of the pressure switch. When it is desired to operate under fixed conditions a non-adjustable orifice can be used with a fixed pressure switch. When it is desired to operate under variable conditions, an adjustable orifice or an adjustable pressure switch can be used or both the orifice and the pressure switch can be adjustable.

The integrator circuit takes the on-off signal generated by the pressure switch and formulates a slowly changing continuous signal therefrom which is fed into the amplifier circuit. The integrator circuit is biased at about +0.6 volts and the signal from the switch increases to about 1.2 volts when the pressure switch is activated and decreases to about +0.0 volts when the switch is deactivated. The integrator circuit produces a gradually decreasing output voltage which feeds into the amplifier when the pressure switch is closed and a gradually increasing voltage when the pressure switch is open. The circuit is constructed of conventional transistors, capacitors and resistors. An example of the circuit will be described hereinafter.

The amplifier circuit receives the signal generated by the integrator circuit and amplifies the signal so that the electric D.C. motor can be controlled at various speeds to insure a constant flow rate of the air stream through the dosimeter. The amplifier circuit amplifies the signal from the integrator to a maximum of about 96% of the total voltage of the power source. For example, for a 5 volt power source, the signal will be amplified to 4.8 volts. Generally, the amplifier has an impedance of greater than 10 ohms and up to 1 megohm. However, an amplifier with an immpedance of less than 10 ohms can be used, e.g., 0.01-10 ohms impedance. The amplifier is constructed by conventional transistors, capacitors and resistors.

The power source usually is a battery of about 5-6 volts. Generally, two nickel cadmium batteries of 4 cells each are used. A direct current power source of rectified A.C. current can also be used.

One optional circuit that can be used in the dosimeter is a battery check circuit. The circuit uses a precision voltage detector which can be adjusted to the voltage of each cell and is set to be activated at the full charge voltage of the battery. A light emitting diode which is activated by a switch is usually used to indicate a full charge of the battery.

Another optional circuit that can be used in the dosimeter is a low air flow detector circuit which is connected to the integrator circuit and is activated when the voltage output of the integrator circuit is at higher than normal operational levels caused by an interruption of the air stream being pumped through the dosimeter. The low flow detector circuit comprises a bistable multivibrator circuit electrically connected to an indicator light such as a light emitting diode.

Another optional circuit that can be used in the dosimeter is a timer circuit. The timer can have both a timing feature to indicate the amount of running time and it can have a pre-set feature to stop the pump at the end of a pre-set time period.

There are two versions of the timing feature required to cover all the various sampling situations. The first is a timer that automatically resets itself to zero at the start of each testing period when the power switch is turned on. The second version is a timer that does not reset when the pump is turned off and on and keeps track of the total cumulative running time. This version of course requires a separate, manual reset switch to perform the resetting function.

Figure 3:
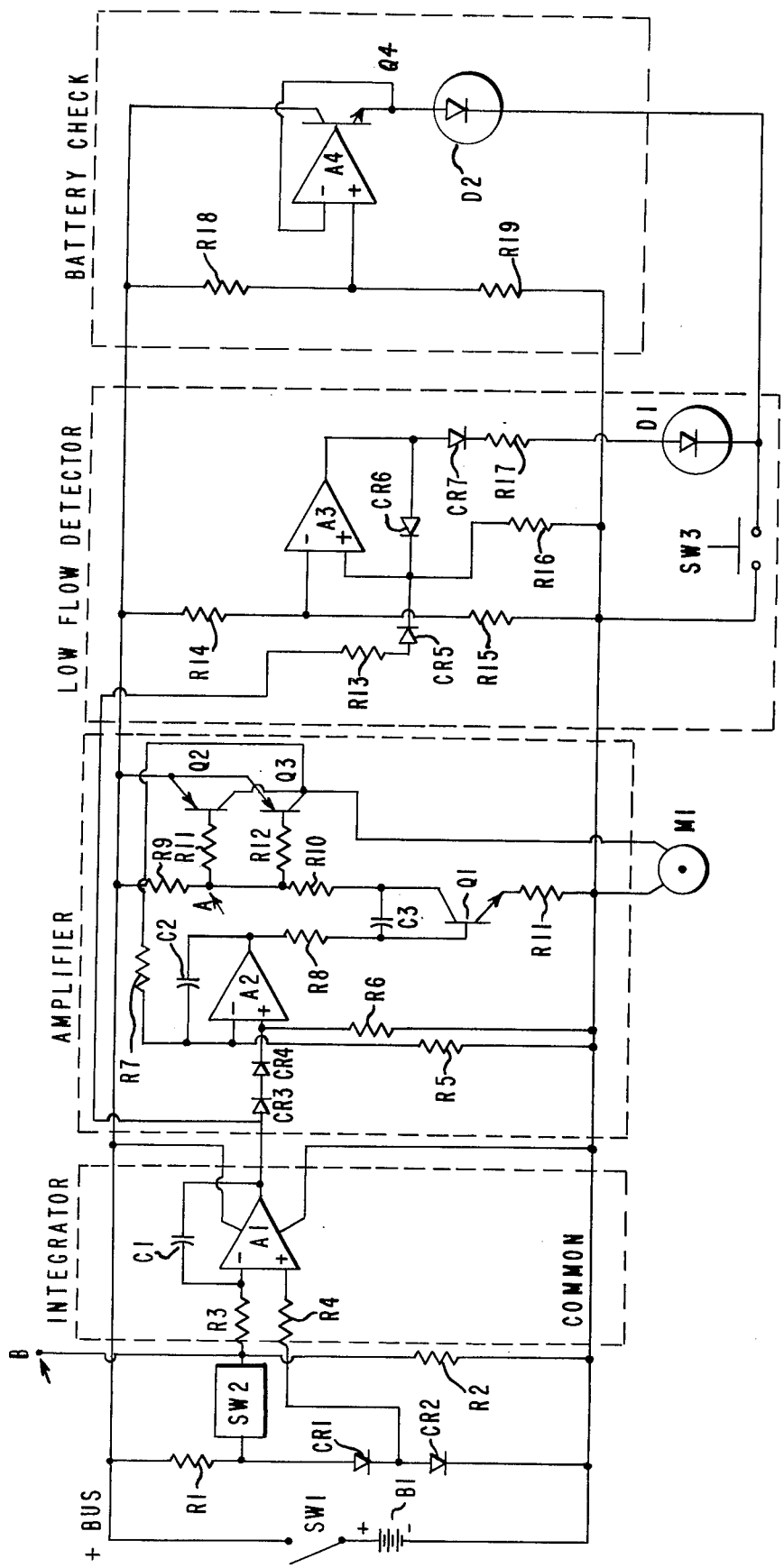
FIG. 3 is a schematic circuit diagram for one preferred embodiment of the dosimeter which contains a low air flow detector circuit and a battery check circuit.

FIG. 3 is a schematic diagram of the pump control system including a pressure switch driving an integrator circuit, an amplifier which drives the pump motor, a low air flow detector circuit and a battery charge indicator.

In FIG. 3, the battery B 1 which supplies power to the circuit has its negative (−) terminal connected to COMMON and its positive (+) terminal connected to power switch SW 1. The other side of SW 1 is connected to the positive (+) BUS.

Amplifier A 1 (which may be operational amplifier such as one of the four amplifiers in a type LM 324 Quad Operational Amplifier) is connected in an integrating configuration with a feedback capacitor C 1 (typically 6.8 microfarads) connected from the out to the inverting (−) input of the ammplifier A 1. The input resistor R 3 (typically 12 megohm) is connected to the inverting input of A 1. The values of R 3 and C 1 determine the integration rate and affect the response of the control circuit. The values are selected to give the best control with a particular pump and differential pulsation filter.

Resistor R 1 (typically 10 K ohms) is connected from the + BUS to one anode of diode, CR 1 (typically type 1N4148) and the cathode of CR 1 is connected to the anode of diode CR 2 (typically type 1N 4148) which has the cathode connected to COMMON. This provides bias voltages of approximately 0.6 volt at the CR 2 anode and 1.2 volts at the CR 1 anode due to the forward voltage drops of the two diodes. The 0.6 volt point is connected to the noninverting input (+) of the amplifier, A 1, to bias the + input at 0.6 volts above COMMON, through a resistor R 4 (typically 12 megohm) which minimizes amplifier offset voltage effects. A resistor R 2 (typically 22 K ohm) is connected from the input resistor R 3 (Point B) to COMMON or ground. This provides 0.0 volts to the input resistor when pressure switch SW 2 is open. SW 2 typically is a pressure switch that operates at 3.0 inches of water pressure. The integrator produces a gradually decreasing voltage at the amplifier output when SW 2 is closed and a gradually increasing voltage when SW 2 is open. The voltage at the amplifier A 1 output is a motor speed signal which when amplified by an amplifier (described hereinafter) determines the pump motor speed. Connection from the + BUS and COMMON are made to A1 to provide power. These connections provide power for A 2, A 3 and A 4.

The motor speed signal is applied to amplifier A 2 (typically ¼ of a type LM 324 through series connected diodes CR 3 and CR 4 (typically IN 4143) to the noninverting (+) input of A 2. Load resistor R6 is connected from the input of A 2 to ground. The amplified signal from the output of A 2 is applied to the base of transistor Q 1 (typically an NPN type 2N2926) through resistor R 8 (typically 10 K ohm). The signal from the collector of Q 1 is applied to the base of parallel connected transistor Q 2 and Q 3 (typically PNP Type 2N5226) through resistor R 10 (typically 100 ohm) connected to point A and through Resistors R 11 and R 12 (typically 100 ohm) connected from point "A" to the transistor bases. The output signal from the common collectors of Q 2 and Q 3 is connected to the pump motor M 1, a variable speed, direct current motor. The other siae of M 1 is connected to COMMON.

The emitter of Q 1 is connected to COMMON through resistor R 11 (typically 220 ohm). Capacitor C 3, (typically 0.01 microfarad) is connected from base to collector Q 1 to reduce noise in the circuit. The emitter of Q 2 and Q 3 is connected to the + BUS. Point "A" is connected to the + BUS through resistor R 9 (typically a 1 K ohm). A feedback resistor R 7 (typically 47 K ohm) is connected from the collectors of Q 2 and Q 3 to the inverting (−) input of A 2 to provide negative feedback. The inverting input of A 2 is connected to COMMON through resistor R 5 (typically 2.2 K ohm).

Resistors R 5 and R 7 determine the overall voltage gain of the circuit from the output of A 1 to the voltage connected to the pump motor. These resistors may be adjusted to provide the optimum balance between fast control response and stable operation in pumps of various characteristics. Capacitor C 2 (typically 0.01 microfarad) is connected from the output of A 2 to the inverting input of A 2 to reduce circuit noise. This connection of A 2, Q 1, Q 2, Q 3 and their associated resistor and capacitors is one of many amplifier circuits suitable for amplifying the motor speed signal from A 1 but this circuit provides a wide voltage range to the motor, typically 0 to 4.8 volts, and provides a constant voltage output preferred in some pump configurations such as where very low motor speed for low flow is required.

The output signal from A 1 varies from about 0 to 1.5 volts during normal control but can increase gradually on up to a saturation level of approximately 3 volts (for a power supply voltage of 4.0 volts) when the pump cannot maintain the required airflow such as when the inlet tube is linked and the airflow is blocked. By detecting when the output of A 1 exceeds 2.5 volts, a low flow detector is provided. Thus, amplifier A 3 (typically ¼ of a LM 324) is connected at its inverting input to a trip voltage level. If a voltage of a greater magnitude than the trip voltage level is applied to the noninverting (+) input of A 3, the output of A 3 will change from the normal level of zero to a high level of approximately 4.8 volts (with a 5 volt power supply).

Resistor R 14 (typically 47 K ohm) is connected from the + BUS to resistor R 15 (typically 22 K ohm). The other side of R 15 is connected to COMMON. The junction between R 14 and R 15 is connected to the inverting (−) input of A 3.

Diode CR 6 (typically a type 1N4148) is connected from the A 3 output to the non-inverting input to keep the A 3 output high even if the original voltage signal is removed. Diode CR 7 (typically a type 1N 4148) resistor R 17 (typically 220 ohm); light emitting diode, D 1 (typically a HP 5082-4484); and a momentary test switch SW 3 are series connected from the output of A 3 to COMMON. When SW 3 is closed with the output of A 3 high, D 1 will light. Amplifier A 3 may be reset to the low output condition by opening switch SW 1 to remove power from the circuit. Resistor R 16 (typically 1.2 meghohm) is connected from the non-inverting input of A 3 to COMMON to assure that A 3 does not inadvertantly go to the high output condition when power is first applied to the circuit. Resistor R 13 (typically a 41 K ohm) is connected from the output of A 1 to the anode of diode CR 5 (typically a type (1N 4148) which is in turn connected to the non-inverting input of A 3 coupling the signal from A 1 into the flow detector circuit. The forward voltage drop of CR 5 helps prevent spurious signals from falsely tripping the low flow detector. In this configuration, the circuit normally requires 20 seconds after flow is interrupted until the circuit trips. This time can be decreased by increasing the ratio of R 14 to R 15.

A battery check circuit is built based on a special light emitting diode, D 2 (typically type HP 5082-4732 manufactured by the Hewlett-Packard Corporation) which lights at a specific level or applied voltage (typically 2.4 volts). Amplifier A 4 (typically ¼ of a type LM 324) has its output driving a transistor Q 4 (typically a 2N 2926). The collector of Q 4 is connected to the + BUS. The emitter of Q 4 is connected to the inverting (−) input of A 4 providing a 1 X gain for signals applied to non-inverting input (+). The emitter of Q 4 is connected to the anode (or + input) of D 2 and the cathode of D 2 is connected to one side of switch SW 3. The other side of SW 3 is connected to COMMON. D 2 will light if SW 3 is closed and the output of A 4 is greater than a trigger voltage (typically 2.4 volts). Resistor R 18 (typically 100 K ohm) is connected from the + BUS to the non-inverting (+) input of A 4 and resistor R 19 (typically 100 K ohm) is connected from the (+) input of A 4 to COMMON. The ratio of R 18 and R 19 can be adjusted to present 2.4 volts to the non-inverting input of A 4 at the desired battery voltage check level, typically 5.15 volts for a battery constructed by connecting four nickel-cadmium rechargeable cells in series.

A timer circuit used to stop the pump after a pre-set period of time could be connected into the previously described integrator circuit at the junction of R3, R4 and SW2 (Point B) of FIG. 3. A positive voltage signal applied at this point causes the integrator to decrease its output and finally the motor, M1, stops.

Figure 4:
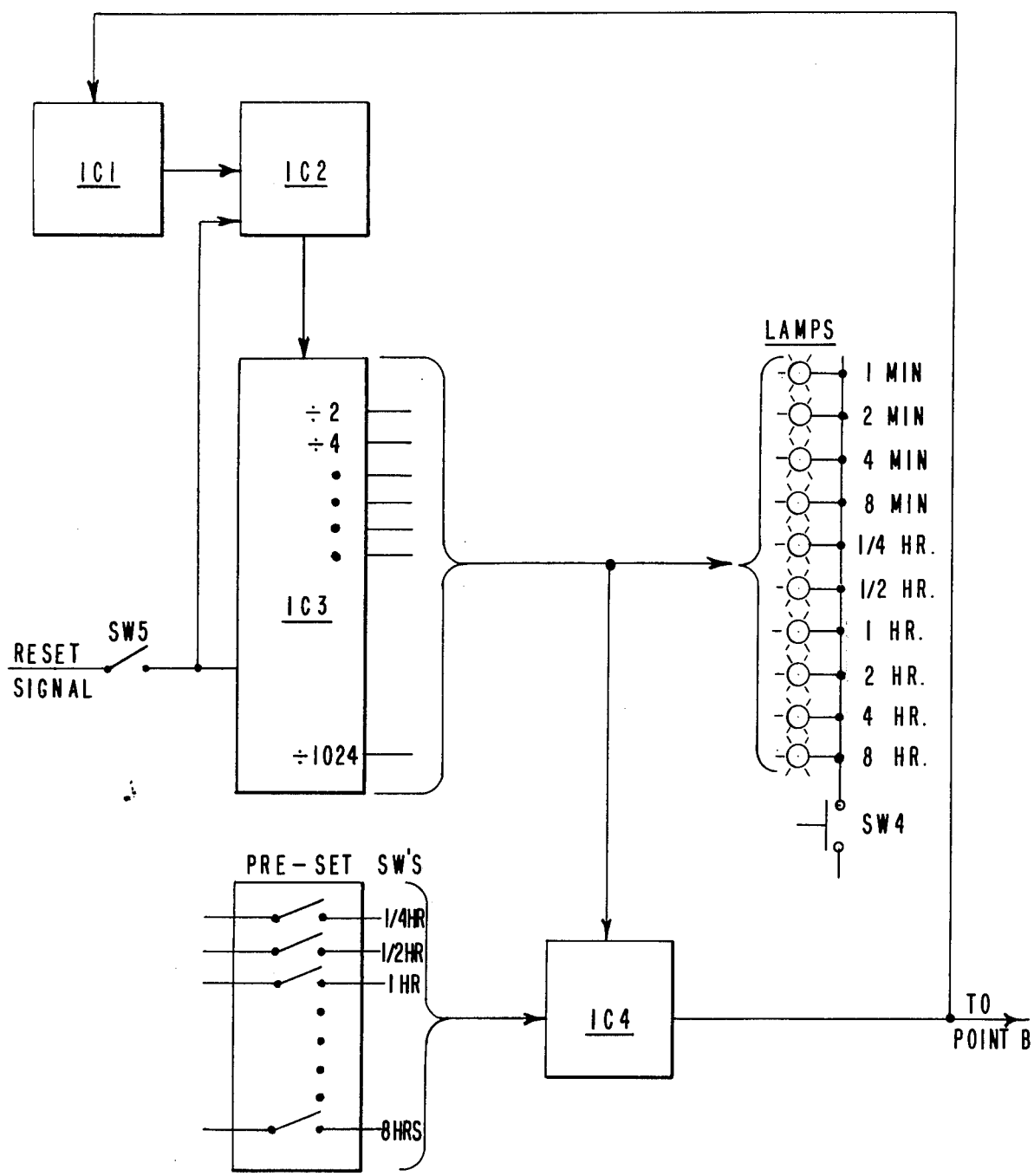
FIG. 4 is a block diagram of a timer circuit.

Circuit designs for solid state, electronic timers suitable for this application are well known and numerous. The circuits can be made of discrete components (such as transistors, resistors, etc.) or from large scales integrated circuits such as used in solid state wrist watches. One practical circuit of a timer with the desired features is shown in FIG. 4, a Digital Timer Block Diagram.

An oscillator, IC1, provides a pulse signal at a typical frequency of 4660 pulses per second as the basis for the timing function. This pulse signal is divided by a prediver, IC2, down to a slower rate such as 128 pulses per hour. This slower signal becomes the input for a second divider IC3, with ten divide-by-two (÷2) outputs.

For the timing function the outputs are connected to a series of ten lamps which are labeled 1 min., 2 min., 4 min., 8 min., ¼ hr., ½ hr., 1 hr., 2 hr., 4 hr., and 8 hrs. The frequency of 128 pulses per hour divided by 2 becomes 64 pulses per hour, which is approximately 1 pulse per minute and is so labeled. The frequency of 64 pulses per hour divided by two becomes 32 pulses per hour, which is approximately 2 pulses per minute and is so labeled and so on, up to 4 pulses per hour, which is 1 pulse in ¼ hour and is so labeled and so on, up to the last output, which is 128 pulses per hour divided by two 10 times (or divided by $2^{10}$ or 1024), which is one pulse in eight hours and is so labeled. A timer so constructed can be read at any time by closing switch SW4 and adding together the values of all the lamps that are lit.

For the pre-set stopping function the outputs from IC3 are also connected to a Concidence Detector Circuit IC4 which is also fed a group of input signals from the pre-set switches. The Coincidence Detector provides a STOP signal output when there is coincidence between the 2 sets of input signals (when the patterns of the two groups of signals exactly match). The STOP signal causes the pump control circuit to integrate down (and stop the pump) and also signals the oscillator to stop.

The dividers IC2 and IC3 are normally reset to zero by a Reset Signal which is generated each time the dosimeter pump is turned "ON." Switch SW5, can be opened and the timer will not reset. This is useful in using the time to totalize a set of time periods. Obviously, the dividers IC2 must be powered by a source separate from the dosimeter pump which would always remain on, if these integrated circuits are the standard type that must always be powered to "remember" the output.

In practical operation of the dosimeter, the dosimeter is placed in an area where workers are operating. Usually an 8 hours work shift is the time period the dosimer is run. At the end of the shift, the circuit is tested to determine if the intake was blocked during the period by observing the light emitting diode (D 1 of FIG. 3) while pressing the momentary switch (SW 3 of FIG. 3). If the diode lights, blockage has taken place during the shift. The filter is then removed from the dosimeter and sent to a laboratory for analysis and the results are recorded. If there is excessive exposure, workers can be withdrawn from the particular area and given another job.

We claim:

1. An improved dosimeter that has an electric motor, a power source, an exhaust port and a filter means in which particles or vapors present in an air stream being pumped through the dosimeter at a controlled constant flow rate are collected on the filter means; the improvement in use therewith comprises a variable drive multicylinder pump, tubularly connected to the filter means and coupled to the electric motor, draws the air stream through the filter means;

an orifice being positioned in a tube attached to the pump and to an exhaust port, wherein the air stream is pumped through the orifice and thereby creates an air pressure drop;

a differential pulsation pressure filter position in a tube connected to the exhaust port and in parallel with the orifice and reduces pulsations in the air stream;

a differential pressure switch positioned in a tube connected in parallel to the differential pulsation filter is activated by a change in the air pressure drop of the air stream and creates a low voltage electrical input signal;

an integrator circuit electrically connected to a power source and to the pressure switch uses the low voltage input signal generated by the pressure switch and integrates this signal;

an amplifier circuit electrically connected to the power source and connected in series to the integrator circuit and to the electric motor which amplifies the signal generated by the integrator circuit and feeds the amplified signal to the electric motor thereby controlling the speed of the motor driving the pump in relationship to the signal generated by the pressure switch to maintain the air stream at a controlled constant flow rate.

2. The dosimeter of claim 1 in which the pump is a multicylinder piston pump.

3. The dosimeter of claim 2 in which the pump is a four-cylinder diaphragm pump.

4. The dosimeter of claim 2 in which the orifice is an adjustable needle valve.

5. The dosimeter of claim 1 in which the pressure switch is activated by an air pressure drop of 3 inches of water and an air pressure drop change of 0.01 to 0.5 inch of water.

6. The dosimeter of claim 1 in which the integrator circuit is biased at about +0.6 volt and the signal from the integrator gradually increases to about +1.2 volts when the pressure switch is activated and gradually decreases to +0.6 volt when the switch is deactivated.

7. The dosimeter of claim 1 in which the amplifier circuit amplifies the signal from the integrator circuit to a maximum of about 96% of the total voltage of the power source and has an impedance of greater than 10 ohms.

8. The dosimeter of claim 1 which has electrically attached to the output of the integrator circuit thereto a low air flow detector circuit comprising a bistable multivibrator circuit electrically connected to an indicator light.

9. The dosimeter of claim 1 which has electrically connected to the power source which is a battery check circuit comprising a precision voltage detector adjusted to the full charge voltage of the battery.

10. The dosimeter of claim 1 which has a timer circuit electrically attached to the power source that indicates the pump operating time and can turn off the pump after a given time interval.

11. The dosimeter of claim 1 in which the pump is a diaphragm pump having four cylinders;

the orifice is an adjustable needle valve which causes an air pressure drop of about 3 inches of water;

the air pressure switch is activated by an air pressure drop change of about 0.1 to 0.5 of water;

the integrator circuit is biased about +0.6 volt and the signal from the circuit gradually increases to about +1.2 volts when the pressure switch is activated and gradually decrases to +0.6 volt when the pressure switch is deactivated;

the amplifier circuit amplifies the signal from the integrator circuit to a maximum of about 96% of the total voltage of the power source and has impedance less than 10 ohms;

the power source is a battery that has a maximum of 5.5 volts and has nickelcadmium cells; and has electrically connected thereto a low flow air detector circuit electrically attached to the output of the integrator circuit comprising a bistable multivibrator circuit electrically connected to an indicator light;

a battery check circuit electrically connected to the power source which is a battery comprising a precision voltage detector adjusted to about 5.2 volts; and a timer circuit electrically attached to the power source that indicates the pump operating time and can turn off the pump after a given time interval.

* * * * *